Nov. 1, 1960 E. S. BOERNER Plant Pat. 1,981
ROSE PLANT
Filed Jan. 27, 1960
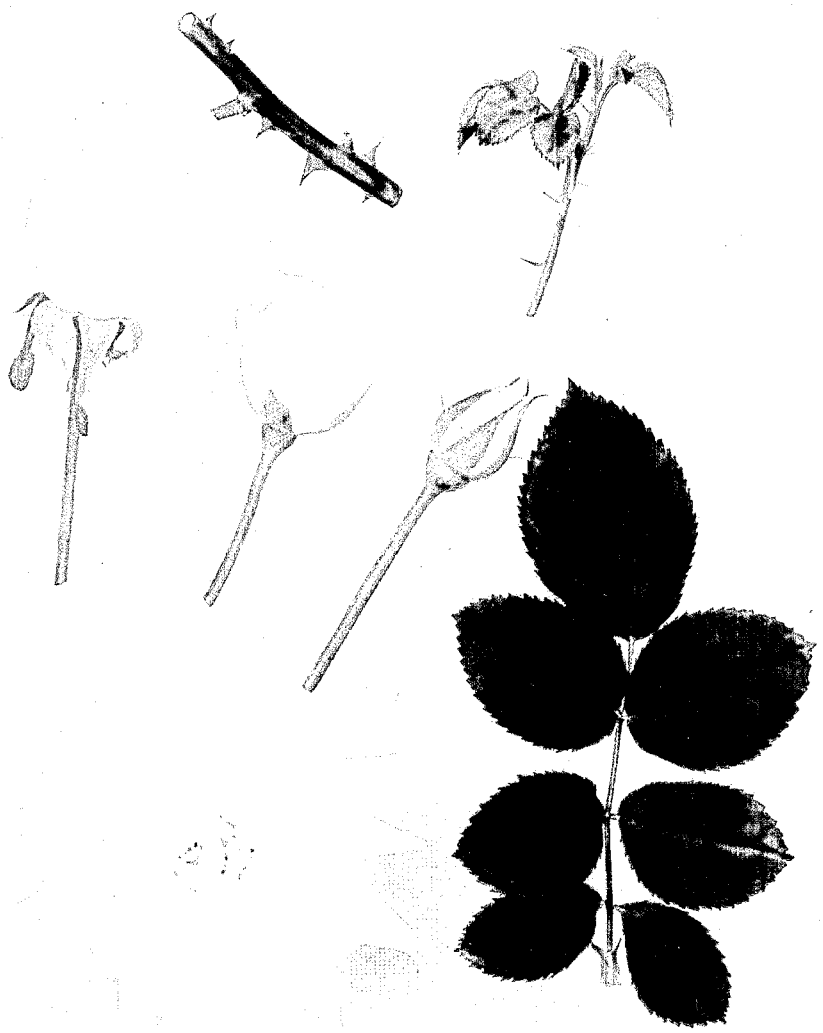
INVENTOR
E. S. Boerner
BY Robb & Robb
ATTORNEYS United States Patent Office Plant Pat. 1,981
Patented Nov. 1, 1960

1,981

ROSE PLANT

Eugene S. Boerner, Newark, N.Y., assignor to Jackson & Perkins Company, Newark, N.Y., a corporation of New York Filed Jan. 27, 1960, Ser. No. 5,083

1 Claim. (Cl. 47—61)

The present invention relates to a new and distinct variety of rose plant of the floribunda class, which was originated by me by crossing the variety "Chic" (Plant Patent No. 1,286) with an unnamed and unpatented White seedling of "Demure" (Plant Patent No. 1,065).

The primary objective of this breeding was to produce a new rose variety which produces white flowers of long-lasting quality suitable for use as cut flowers, as grown in the greenhouse. This objective was fully achieved by crossing the two parent varieties referred to above, both of which are endowed with long-lasting flower qualities. In addition, other desirable improvements were attained, as evidenced by the following unique combination of characteristics which are outstanding in the new variety and which distinguish it from its parents, as well as from all other varieties of which I am aware:

(1) Well-shaped, full-bodied flower buds which are excellent for cut flower purposes;

(2) Large number of flower petals which open into very attractive flowers of good form;

(3) Long-lasting quality of the flowers; and (4) A distinctive White general color tonality.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
- *Seed parent.*—"Chic."
- *Pollen parent.*—An unnamed White seedling of "Demure."

Classification:
- *Botanic.*—"Floribunda."
- *Commercial.*—"Floribunda."

*Flower*

(Observations made from specimens grown in a greenhouse at Newark, New York, near the middle of August.)

Blooming habit: Recurrent—continuous.

Bud:
- *Size.*—Medium.
- *Form.*—Ovoid; full-bodied; is not affected by wet or hot weather.
- *Color.*—When sepals first divide—Sea-Foam Yellow, Plate 31. When petals begin to unfurl—White, Plate 53, lightly overcast with Sea-Foam Yellow, Plate 31. When half-blown: inside of petals—White, Plate 53; reverse of petals—White, Plate 53.
- *Sepals.*—Branched; curl back when petals begin to unfurl. Color: inside—Malachite Green, Plate 31; outside—Bice Green, Plate 17.
- *Calyx.*—Color—Bice Green, Plate 17. Shape—pear. Size—long. Aspect—smooth. Odor when rubbed—none.
- *Peduncle.* — Length — long. Aspect — rough. Strength—erect; heavy. Color—Bice Green, Plate 17.
- *Opening.*—Opens up well; is not affected by adverse weather conditions.

Bloom:
- *Size.*—Medium. Average size when fully expanded—3 inches.
- *Borne.*—Several together.
- *Stems.*—Long; strong.
- *Form (when first open).*—Cupped. Permanence—retains its form to the end, but outer petals curl back.
- *Petalage.*—Double (full but open center). Number of petals under normal conditions—from 45 to 50.
- *Color.*—Center of flower—White, Plate 53. Outer petals—White, Plate 53. Base of petals (aiglet)—Sulphur Yellow, Plate 5. Inside of petals—White, Plate 53. Reverse of petals—White, Plate 53. General tonality from a distance—White, Plate 53.
- *Discoloration.*—General tonality at end of first day—White, Plate 53. Second day—White, Plate 53. Third day—White, Plate 53.

Petals:
- *Texture.*—Leathery; is not affected by wet or hot weather.
- *Appearance.*—Inside—satiny. Outside—shiny.
- *Form.*—Oval.
- *Arrangement.* — Imbricated (regularly arranged shingle-like).
- *Petaloids in center.*—Few; small.
- *Persistence.*—Drop off cleanly.
- *Fragrance.*—Moderate. Nature—tea (average hybrid tea scent).
- *Lasting quality.*—On the plant—very long. As cut flower—very long.

*Genital organs*

Stamens, anthers: Small; many; regularly arranged around styles. Color—Naples Yellow, Plate 16.

Stamens, filaments (threads): Medium length. Color—Sulphur Yellor, Plate 5.

Pollen: Color—Cream Color, Plate 16.

Styles: Bunched; uneven length; medium length; thin.

Stigmas: Color—Naphthalene Yellow, Plate 5.

Ovaries: All enclosed in calyx.

Hips: None.

Seeds: None.

*Plant*

Form: Bush.

Growth: Vigorous; branching.

Foliage: Compound of 3 to 7 leaflets.
- *Size.*—Large.
- *Quantity.*—Abundant.
- *Color.*—New foliage: upper side—Light Bice Green, Plate 17, lightly overcast with Oxblood Red, Plate 1; under side—Courge Green, Plate 17, lightly overcast with Van Dyke Red, Plate 13. Old foliage: upper side—Varley's Green, Plate 18; under side—Light Bice Green, Plate 17.
- *Shape.*—Oval pointed.
- *Texture.*—Upper side—leathery. Under side—smooth.
- *Ribs and veins.*—Ordinary.
- *Edge.*—Serrated (saw-toothed).
- *Serration.*—Double; small.

*Leaf stem.*—Color—Jade Green, Plate 31. Under side—prickly.

*Stipules.*—Medium length; smooth.

Wood:

*New wood.*—Color—Absinthe Green, Plate 31. Bark—smooth.

*Old wood.*—Color—Cress Green, Plate 31. Bark—smooth.

Thorns:

*Thorns.*—Quantity: on main stalks from base—ordinary; on laterals from stalk—ordinary. Form—narrow base; medium length; straight. Color (when young)—Eugenia Red, Plate 13. Position—irregular.

*Prickles*—Quantity: on main stalks—none; on laterals—none.

*Short needles.*—Quantity: on main stalks—none; on laterals—none.

I claim:

A new and distinct variety of rose plant of the floribunda class, substantially as herein shown and described, characterized particularly as to novelty by the unique combination of well-shaped, full-bodied buds which are especially suited for cut flowers as grown in the greenhouse, the large number of flower petals which open into very attractive flowers of good form, the long-lasting quality of the flowers, and the distinctive White general color tonality of the flowers.

No references cited.